United States Patent [19]

Berg

[11] Patent Number: 4,603,980

[45] Date of Patent: Aug. 5, 1986

[54] METHODS OF MEASURING TEMPERATURE AND ELECTRICAL RESISTIVITY IN A MOLTEN GLASS STREAM

[75] Inventor: James I. Berg, Granville, Ohio

[73] Assignee: Owens-Corning Fiberglas Corporation, Toledo, Ohio

[21] Appl. No.: 761,997

[22] Filed: Aug. 2, 1985

Related U.S. Application Data

[63] Continuation-in-part of Ser. No. 576,841, Feb. 3, 1984, abandoned.

[51] Int. Cl.[4] .................. C03B 5/24; G01K 7/02; G01N 27/14
[52] U.S. Cl. ............................ 374/179; 65/29; 324/65 P; 374/142
[58] Field of Search ............... 374/170, 186, 143, 179; 358/113; 65/29, 158, 162; 324/65 R

[56] References Cited

U.S. PATENT DOCUMENTS

| | | | |
|---|---|---|---|
| 2,679,749 | 6/1954 | Poole | 65/134 X |
| 2,988,690 | 6/1961 | Love et al. | 324/64 X |
| 3,278,844 | 10/1966 | Bell et al. | 324/65 R |
| 3,339,138 | 8/1967 | Baker et al. | 324/64 |
| 3,374,430 | 3/1968 | Lode | 324/64 |
| 3,606,792 | 2/1969 | Yoshimoto | 374/179 |
| 4,038,532 | 7/1977 | Burris et al. | 374/143 X |
| 4,277,274 | 7/1981 | Chrisman | 65/29 |
| 4,363,929 | 12/1982 | Bollen | 374/179 |
| 4,428,686 | 1/1984 | Bray | 374/179 |
| 4,519,830 | 5/1985 | Wolak | 65/162 |

Primary Examiner—Daniel M. Yasich
Attorney, Agent, or Firm—Ronald C. Hudgens; Robert F. Rywalski; Francis D. Thomson

[57] ABSTRACT

A small sensor electrode with only the tip exposed is used with a much larger return electrode to complete a high frequency circuit through molten glass. The sensor electrode is calibrated in the laboratory and then used to measure the resistivity of the molten glass. This sensor electrode consists of a type R thermocouple with which one can also measure the temperature of the thermocouple junction. Thus one can measure both the temperature and the resistance at a common point. These measurements are used to monitor the molten glass system.

4 Claims, 3 Drawing Figures

METHODS OF MEASURING TEMPERATURE AND ELECTRICAL RESISTIVITY IN A MOLTEN GLASS STREAM

CROSS REFERENCE TO RELATED APPLICATIONS

This is a continuation-in-part of co-pending application Ser. No. 576,841 filed Feb. 3, 1984 now abandoned.

This invention pertains to measuring molten glass electrical resistivity.

In one of its more specific aspects, this invention pertains to the simultaneous measurement of the temperature and the electrical resistivity of a molten glass stream at a common point.

BACKGROUND OF THE INVENTION

Knowledge of electrical resistivity of glass in a production melter or channel would be very useful. In an electric melter the resistivity controls power dissipation. In either a gas or electric melter the monitoring of any quality relating to glass composition, and thus to viscosity, could signal possible upset conditions in time to make compensating adjustment in the subsequent forming operations.

The sophistication and sensitivity of most laboratory apparatus prohibit application in the hostile field environment. To minimize the effect of temperature variations, any physical property measurement in a melter should be confined to a small region. The device of this invention measures both resistivity and temperature near the center of a very small sample of glass.

The resistance is the ratio of voltage, or potential drop, to current across some part of a circuit. In an electrolyte such as molten glass, the distribution of potential can be controlled by the design of the electrodes. Of particular significance is the fact that an extreme disparity in sizes of the electrodes serves to concentrate the major portion of the potential very close to the smaller electrode. In the limiting case, the nature of the larger electrode and the separation distance become irrelevant, the net resistance depending only on the geometry of the small electrode and the resistivity of the electrolyte. A small, 2 mm to 10 mm diameter, sensor electrode and a much larger return electrode which has a surface area of at least 100 times that of the sensor electrode are used to complete a high frequency circuit through the molten glass. Thus, this single small sensor electrode can be calibrated in a laboratory solution of known resistivity, and then used to measure the resistivity of another electrolyte. The measurement of the resistivity is independent of the amount of fluid or size or geometry of either container or the size and shape of the return electrode.

The sensor electrode consists of a type R (platinum versus platinum—13 percent rhodium) thermocouple junction in contact with the bottom of a double bore alumina tube. The sensor electrode is constructed of heavy wire to minimize resistance. The small size and structural simplicity of the electrode make insertion into a furnace or glass melt relatively easy. There are no mechanical parts in the electrodes to be affected by the molten glass or high temperature. The sampled region in the resistivity measurement is nearly a sphere a few centimeters in diameter centered at the sensor electrode. A high frequency is used to eliminate polarization and interference from other electrical sources. By using the sensor electrode as a thermocouple, temperature is measured at the common location the resistivity was measured at.

DESCRIPTION OF THE PREFERRED EMBODIMENT

Figure 1:
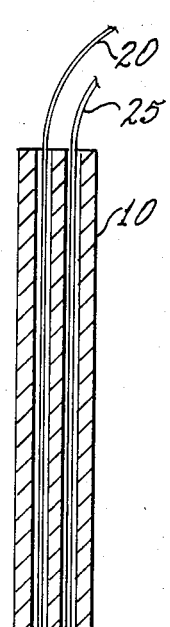
FIG. 1 is a cross section of the sensor electrode.

FIG. 1 shows the sensor electrode which is enclosed in a tube 10 except for the junction 30. This tube thereof is made from a material which will withstand the corrosive effects of being emerged in a molten glass mass. Alumina is a satisfactory material. A suitable size for this tube is 1 to 10 mm in diameter and from 20 to 200 cm in length. Only the bottom few inches is inserted into the molten glass mass. By construction, the device is an exposed-tip type R thermocouple in which only the junction is exposed to the molten glass mass.

Figure 2:
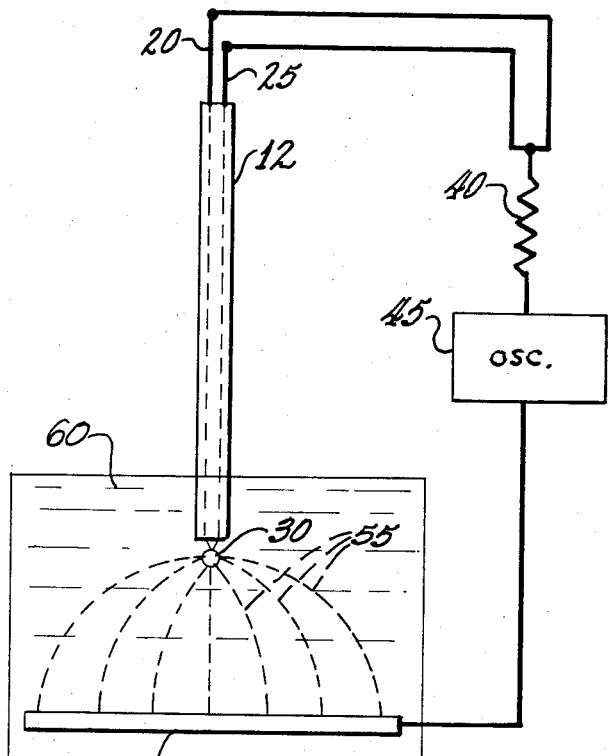
FIG. 2 is an elementary circuit diagram.

In FIG. 1 the alumina tube 10 and shown as "12" in FIG. 2 contains the R thermocouple with platinum with 13% rhodium wires 20 and platinum wires 25 connected at the electrode junction 30. FIG. 2 shows by an elementary circuit diagram, how one obtains resistivity information in addition to temperature. The electrodes 30 and 50 are positioned in the molten glass 60. The circuit has a standard resistance 40 and as the signal generating means a 1 KHz oscillator 45 built in. An example of this oscillator would be a Function Generator/Oscillator made by Hewlett-Packard, Model HP310A. The high frequency circuit through the glass is completed by use of a much larger return electrode 50. Because the sensor electrode is much smaller than the sensor electrode there is an extreme disparity in size between this pair of electrodes, therefore the electric field lines 55 converge at the sensor electrode, with the result that most of the potential drop in the glass occurs very close to the sensor. Two important consequences of this are (a) the resistivity and temperature are measured at the same geometrical point, and (b) the nature and position of the return electrode are unimportant. Thus, one may use any convenient metallic object, such as a skimmer or thermocouple sheath, as the return electrode.

The sensor electrode, is calibrated at room temperature in a 0.1N KCl aqueous solution, using a long wire as the return electrode. The calibration constant is in very good agreement with calculations from electrostatic theory for a small electrode coupled to a much larger one.

The advantage of measuring both resistivity and temperature at the same point is that the resistivity signal may be compensated for local temperature variations, which inevitably will occur under production conditions.

Figure 3:
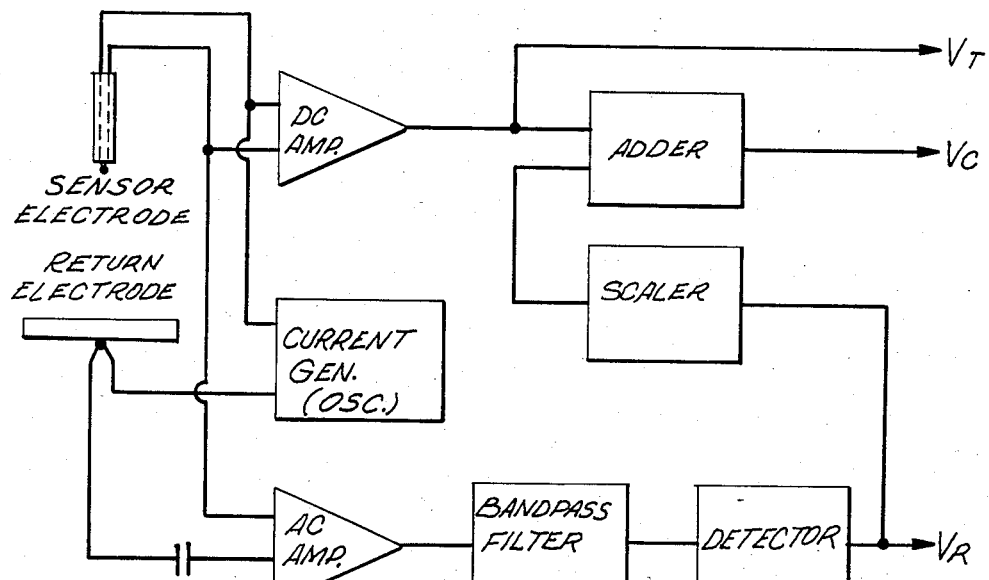
FIG. 3 is a schematic drawing of the analog circuit used.

FIG. 3 indicates schematically the analog circuit employed in production use. An example of a suitable current generator would be a Burr-Brown, Model 4423. The four-lead arrangement (two to each sensor electrode and the return electrode) eliminates lead resistances. The output voltage, $V_T$, is proportional to temperature, while $V_R$ is proportional to resistance. The signals are scaled and added, yielding a voltage, $V_C$, which is sensitive only to composition-induced resistivity changes, and not to those induced by local temperature variations. Isolation amplifiiers and power supplies can be used.

The algebraic relationship between the incremental voltages where the scaling constant, H, is chosen give an output translatable, through the thermocouple calibration, to equivalent temperature is shown by:

$$\Delta V_C = H \Delta V_R + \Delta V_T$$

Where $$H = T^2 / M A_P (V_R + V_O)$$

Here, T is absolute temperature in degrees Kelvin, M is the ratio of temperature to voltage change for the thermocouple, $A_P$ is the resistivity activation temperature for the glass, $V_R$ is the resistance amplifier output voltage, and $V_O$ is the offset voltage in the resistance-voltage linear relationship. Only $V_R$ changes with sensor calibration, and this can be measured with the sensor in place after installation. Thus, no laboratory calibration is necessary.

A small electrode has relatively large characteristic impedance. Thus, minute currents can give rise to relatively large voltage signals. This fact is used to advantage in resistivity measurement, where a small oscillator current produces an easily measurable voltage.

EXAMPLE 1

A sensor electrode was prepared by placing a R type thermocouple in an alumina tube and sealing the bottom with insulating cement so only the thermocouple junction was left exposed as in FIG. 1. The alumina tube was approximately 7 mm in diameter and 1 meter long. This tube was inserted into the molten glass stream 40 cm from the return electrode which, in this case, was the skimmer which was much larger than the sensor electrode. A sinusoidal current source was applied to the electrodes. The voltage developed across the electrodes, proportional to resistivity, was amplified by a phase-lock amplifier and filtered through tuned circuits. Then it was rectified using a synchronous detector. The phase-lock amplifier and synchronous detector received a signal directly from the oscillator. The arrangement is known commercially as a "lock-in amplifier." The thermocouple signal was treated separately, and in the conventional manner was amplified, corrected for cold-junction variations, and filtered before the temperature readings were taken.

I claim:

1. A method of measuring the temperature and electrical resistivity of a molten glass stream using a signal generating means, a signal detector means with the improvement comprising: measuring simultaneously at substantially the same location the temperature and the electrical resistivity of said glass stream by using a pair of electrodes with extreme disparity in sizes between said pair of electrodes with a sensor electrode of said pair of electrodes having a diameter of 2 mm to 10 mm, a return electrode of said pair of electrodes having a surface area of at least 100 times that of said sensor electrode, said sensor electrode comprising as the conductor wires of a thermocouple having only the junction exposed to contact with said molten glass stream and with a signal sent from said signal generating means through said pair of electrodes to said detector means.

2. The method of claim 1 in which the thermocouple junction is a type R thermocouple.

3. The method of claim 1 in which the sensor electrode is 20 cm to 200 cm from the return electrode.

4. The method of claim 1 in which the main body of the sensor electrode is an alumina tube.

* * * * *